United States Patent [19]
Moody

[11] Patent Number: 5,095,792
[45] Date of Patent: Mar. 17, 1992

[54] DEVICE FOR CUTTING MICROHEMATOCRIT TUBES

[76] Inventor: Ernest Moody, 6194 Pick Wick Rd., Tallahassee, Fla. 32208

[21] Appl. No.: 745,817

[22] Filed: Dec. 4, 1989

[51] Int. Cl.$^5$ .............................................. B26D 5/38
[52] U.S. Cl. ......................................... 83/372; 83/54; 83/167; 83/444; 83/648; 83/953
[58] Field of Search ................... 83/54, 372, 167, 444, 83/575, 582, 588, 648, 929, 944, 953, 468.6

[56] References Cited

U.S. PATENT DOCUMENTS

| | | | |
|---|---|---|---|
| 2,798,548 | 7/1957 | Leirer | 83/372 X |
| 3,469,750 | 9/1969 | Vanderbeck | 83/167 X |
| 3,785,233 | 1/1974 | Robinson | 83/167 |
| 4,579,029 | 4/1986 | Sunaga | 83/372 X |

Primary Examiner—Frank T. Yost
Assistant Examiner—Eugenia A. Jones
Attorney, Agent, or Firm—Joseph C. Mason; Ronald E. Smith

[57] ABSTRACT

A table top machine of box-like construction has a cutting mechanism in its interior and an entry bore that receives a microhematocrit tube. In a first embodiment, the end of a tube inserted into the machine closes a switch that activates the cutting mechanism so that tubes are always cut in the same place, without regard to the ratio of linear space in the tube occupied by red blood cells, clotted blood cells and clear plasma or serum. In a second embodiment, a photoelectric cell positioned at the inner end of the entry bore triggers the cutting mechanism when the end of the tube filled with red or clotted blood cells has passed the eye. Thus, tubes are cut at differing positions along the extent of the tube, depending upon how much each tube is filled with red blood cells or clotted blood cells and how much is filled with clear plasma or serum.

3 Claims, 6 Drawing Sheets

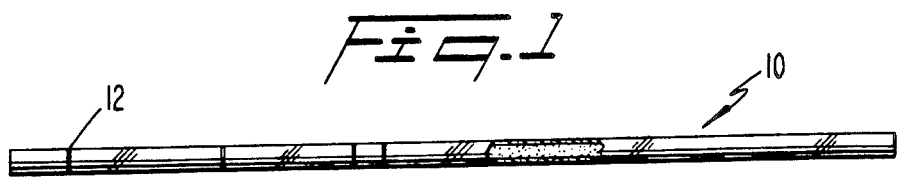
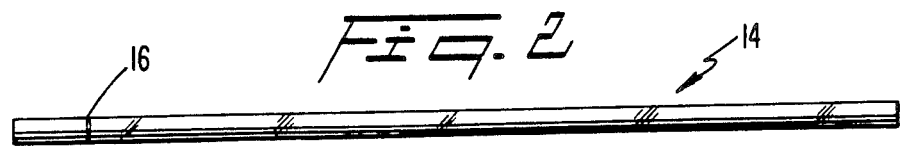
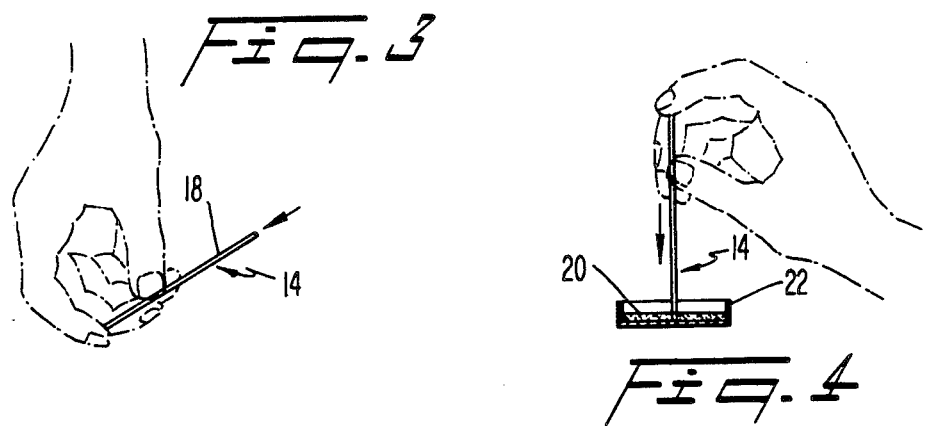
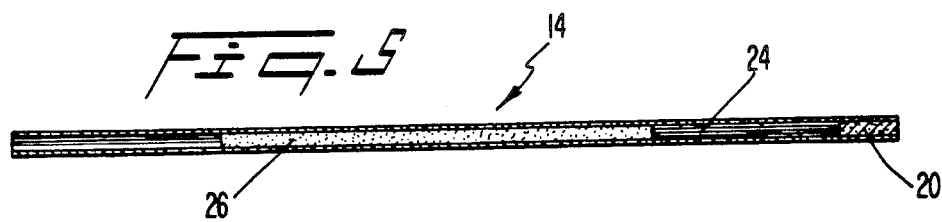
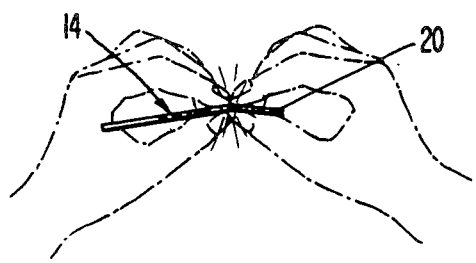
Fig. 6 PRIOR ART

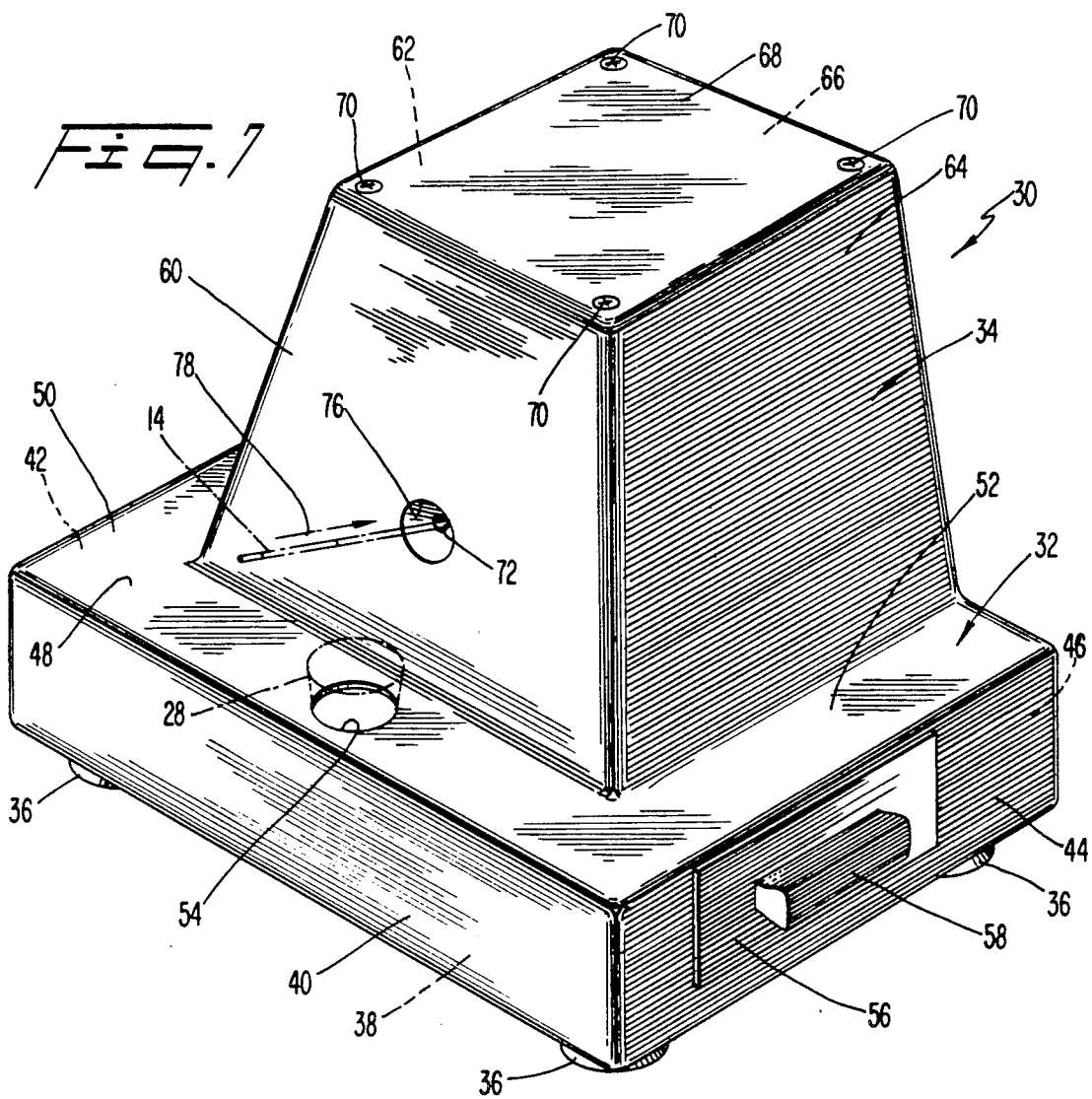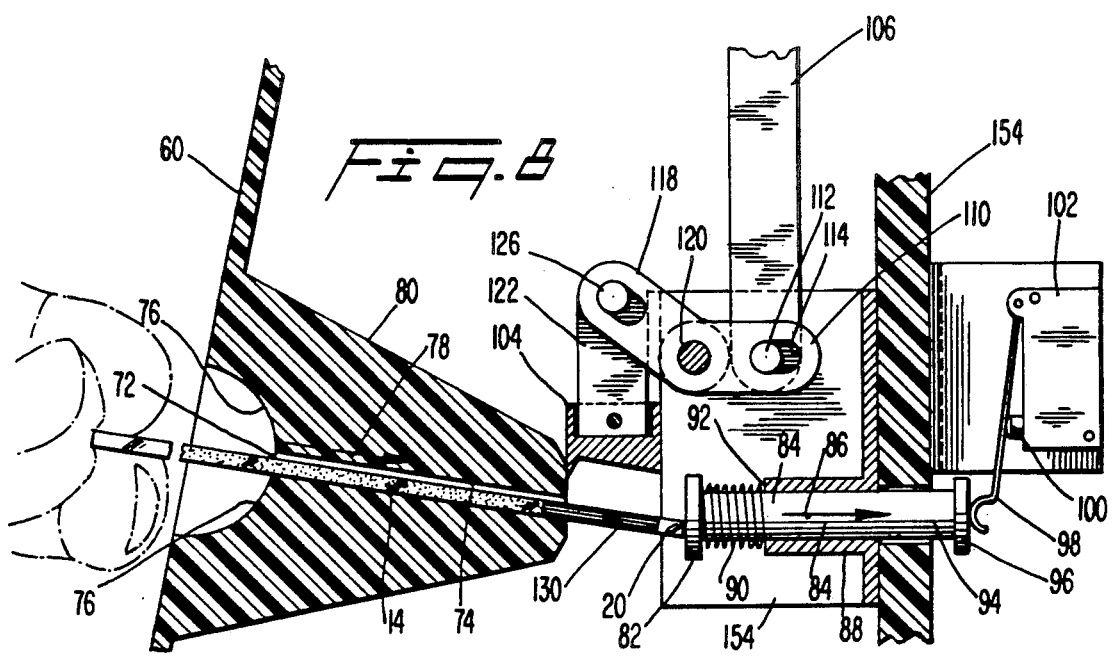

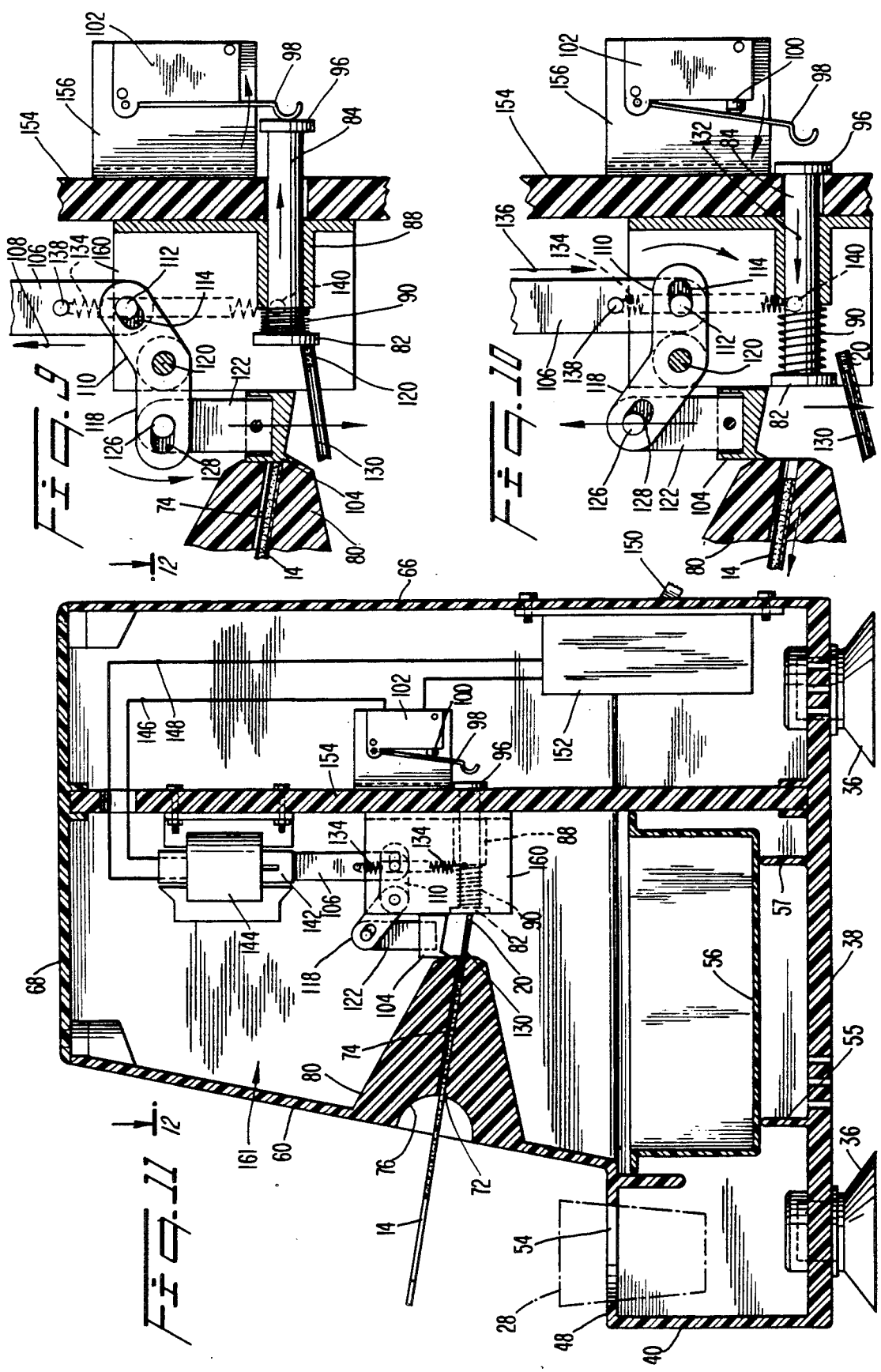

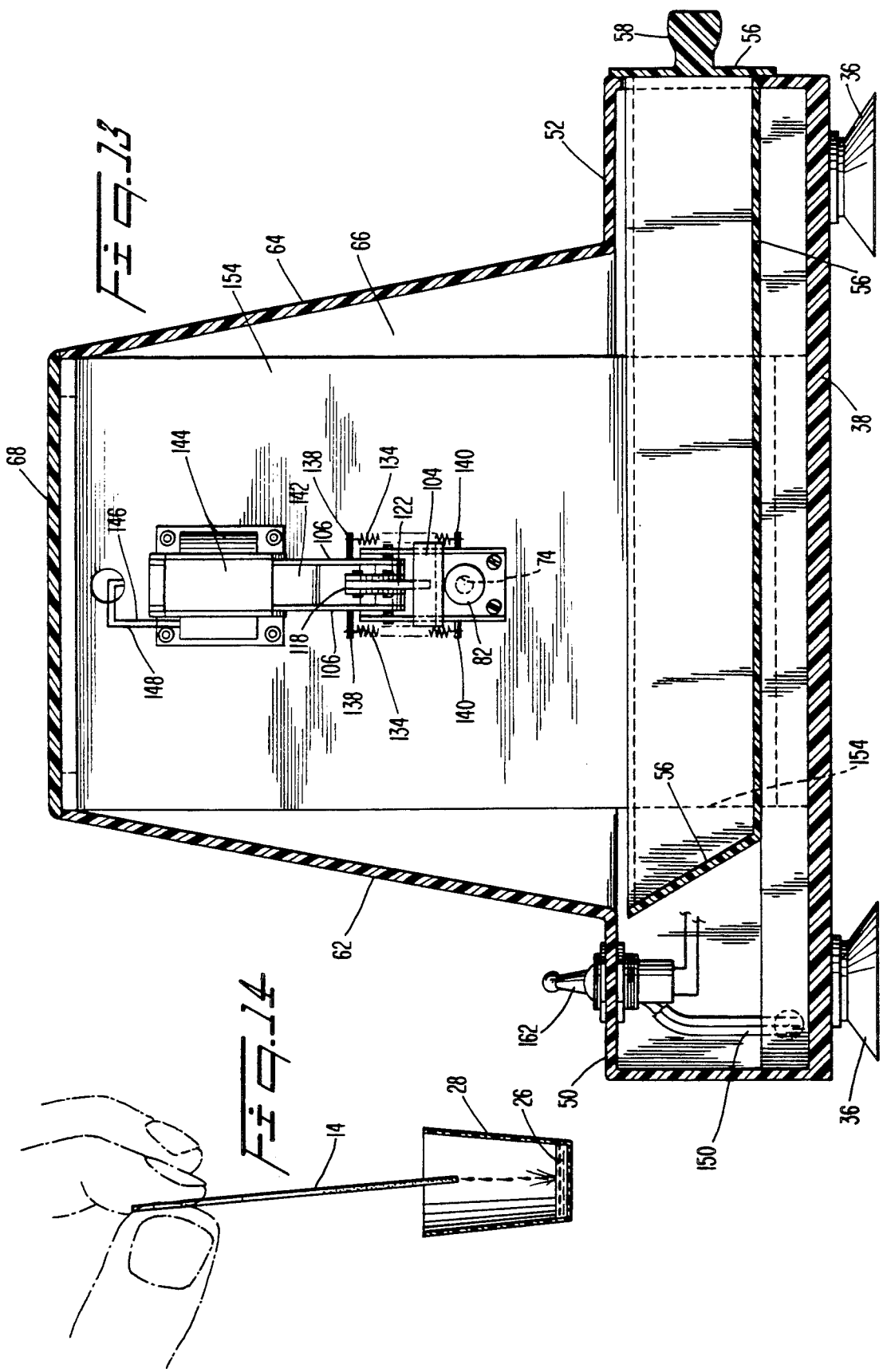

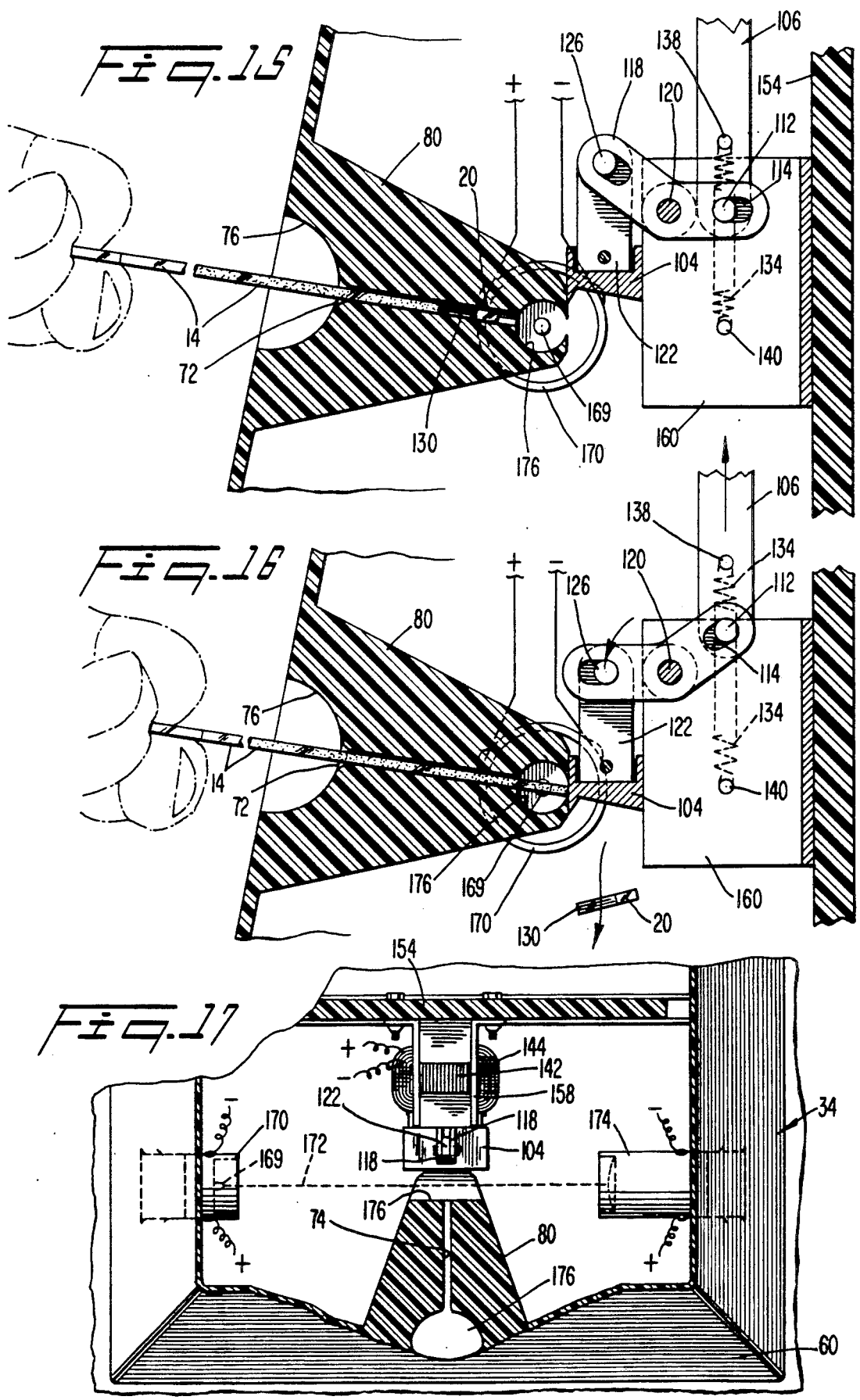

DEVICE FOR CUTTING MICROHEMATOCRIT TUBES

TECHNICAL FIELD

This invention relates, generally, to an electro mechanical device having utility in connection with the cutting of microhematocrit tubes. More particularly, the device cuts the tube at an optimal location to maximize the amount of plasma that may be collected for a blood test.

BACKGROUND ART

Microhematocrit tubes are very small diameter tubes that draw blood thereinto by capillary action. They are used to draw blood from newborn infants or other individuals whose medical condition is such that the amount of blood given by them for test purposes must be held to a minimum.

To draw a minimal amount of blood from such a patient, a small prick is made to break the skin and permit a nominal amount of bleeding. The tube is held to the location of the prick and a small amount of blood is drawn thereinto by the phenomenon of capillary action.

The tube is taken to the lab and placed into a centrifuge; red blood cells or clotted blood cells are drawn to the bottom of the tube and clear plasma or serum, having a lower specific gravity than the cells, fills the balance of the tube. In many tests, the red blood cells or clotted blood cells are not needed and they are discarded. In these tests, only the clear plasma or serum is retained.

Most lab technicians score the tube with a file at the point where it is to be broken and then they manually break the tube; some dispense with the scoring and simply break the tube without first weakening it. Both of these methods are unsatisfactory because small droplets of blood and small shards of glass are produced by such breaking. The droplets of blood may be so small that they are suspended in air and may be aspirated by the medical personnel working in the room. Since blood may carry fatal diseases, a need exists for a better method of breaking microhematocrit tubes.

DISCLOSURE OF INVENTION

The need for a safe means of breaking microhematocrit tubes is provided in the form of a table top device, of parallelepiped construction, having an entry bore and a tube cutting mechanism in its substantially hollow interior. The medical technician, holding a finger over an open end of the tube to be broken, inserts the free end of the tube into the entry bore.

In a first embodiment, the leading end of the tube activates a switch which activates a solenoid which in turn triggers a cutting mechanism that cuts off the end of the tube.

In a second embodiment, a photoelectric eye activates that cutting mechanism when the red blood cells or clotted blood cells collected at the bottom of the tube have passed the eye, i.e., the eye detects the presence of the clear plasma or serum collected atop the red or clotted blood cells. In this manner, practically every tube is cut at a different location along its extent because the number of red blood cells or clotted cells collected at the bottom of the tube varies from patient to patient.

It is therefore understood that a primary object of this invention is to provide a microhematocrit tube cutter that protects medical personnel in the room where the cutting takes place.

A closely related object is to provide a table top apparatus that performs the cutting in a cost efficient manner.

Additional objects will become apparent as this description proceeds.

The invention accordingly comprises the features of construction, combination of elements and arrangement of parts that will be exemplified in the constructions set forth hereinafter and the scope of the invention will be set forth in the claims.

BRIEF DESCRIPTION OF DRAWINGS

For a fuller understanding of the nature and objects of the invention, reference should be made to the following detailed description, taken in connection with the accompanying drawings, in which:

FIG. 1 is an elevational, partially broken away view of a first type of microhematocrit tube;

FIG. 2 is an elevational view of a second type of microhematocrit tube;

FIG. 3 is a perspective view showing how the tube of FIG. 1 or FIG. 2 is held after a blood sample has been collected;

FIG. 4 is a perspective view showing how the free end of the tube is plugged with clay prior to centrifuging;

FIG. 5 is a longitudinal sectional view of a tube that has undergone centrifuging;

FIG. 6 is a perspective view showing the prior art method of breaking microhematocrit tubes;

FIG. 7 is a perspective view of an illustrative embodiment of the invention;

FIG. 8 is the first fig. in a sequence of three figs. showing the operation of the cutting blade member and associated mechanism in animation;

FIG. 9 is the second of said figs.;

FIG. 10 is the third of said figs.;

FIG. 11 is a sectional view taken along line 11—11 in FIG. 12;

FIG. 13 is a sectional view taken along line 13—13 in FIG. 12;

FIG. 14 is a view showing how the tube is emptied after its end has been cut off by the novel device;

FIG. 15 is the first of three figs. that show in animation how the cutting blade member of the second embodiment is operated by a photoelectric eye means;

FIG. 16 is the second fig. in said series of figs.; and

FIG. 17 is the third fig. in said sequence of figs.

Similar reference numerals refer to similar parts throughout the several views of the drawings.

BEST MODES FOR CARRYING OUT THE INVENTION

Figure 12:
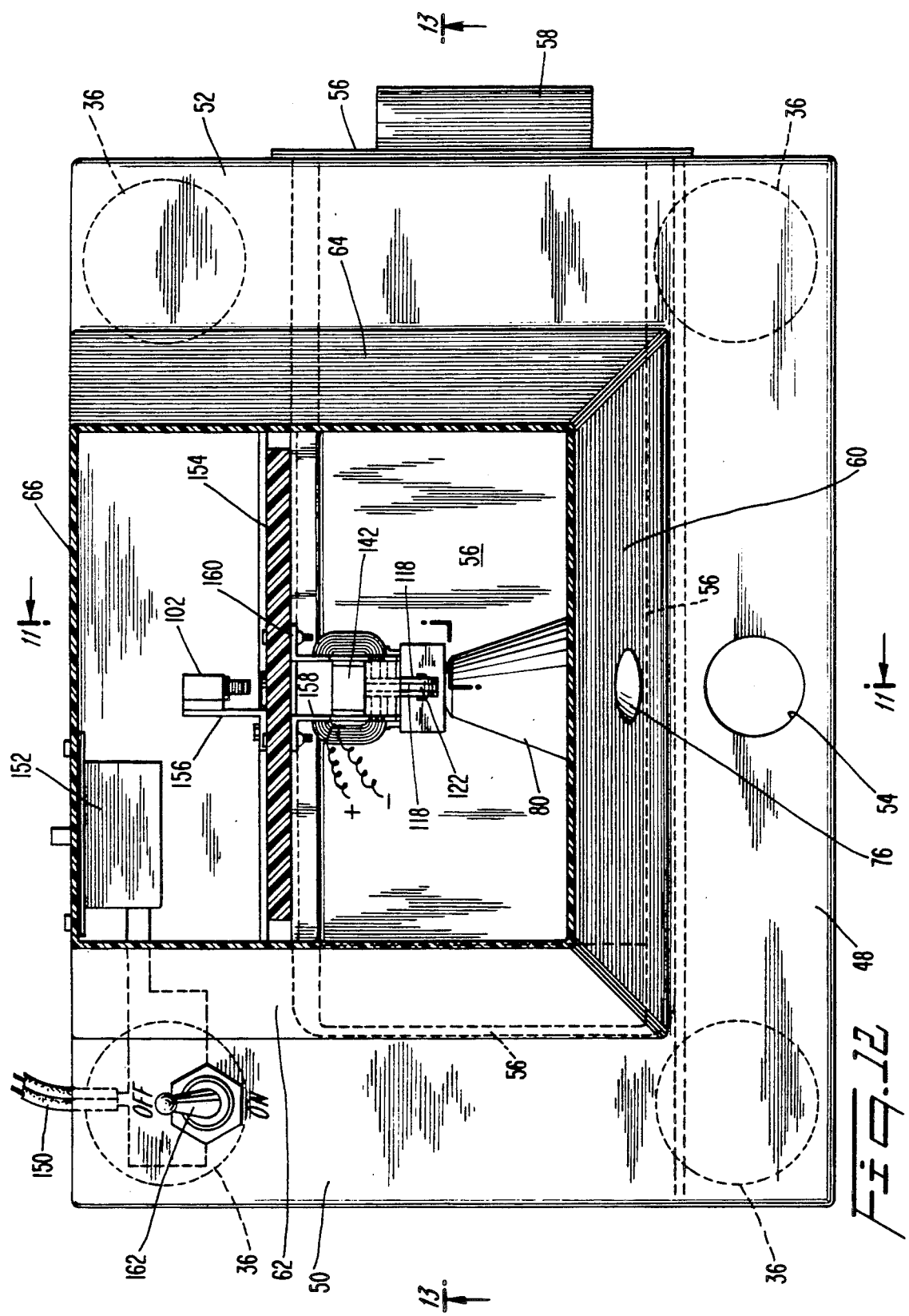
FIG. 12 is a sectional view taken along line 12—12 in FIG. 11.

FIG. 1 depicts a microhematocrit tube 10 of the heparinized type, i.e., the tube of FIG. 1 has been treated with heparine to keep blood drawn thereinto in a nonclotted state; it has a red strip 12 at its top end to identify it. Tube 10 is preferably of glass construction as indicated by the broken away part of FIG. 1.

Since blood drawn into tube 10 will not clot, said blood separates into red blood cells and serum when centrifuged.

FIG. 2 depicts a non-heparinized tube 14, identified as such by its blue top 16. Blood drawn into it will clot and, when centrifuged, the heavy clotted blood will be drawn towards the bottom of the tube and the lighter serum will overlie the clotted blood, i.e., the serum becomes the supernatant.

As depicted in FIG. 3, blood 18 is temporarily retained in tube 14 by atmospheric pressure immediately after the blood sample has been taken, i.e., the technician's finger caps an open end of the tube as shown. Next, as depicted in FIG. 4, the free end of the tube is inserted into a thin layer of clay 20 in dish 22 to plug said free end, i.e., the clay serves as a stopper means. Tube 14 (or tube 10) is then placed in a centrifuge, not shown; as shown in FIG. 5, clotted blood cells and other cellular debris 24 will collect in the bottom, plugged end of the tube and clear serum or plasma 26 will collect in the top, open end thereof.

Since only the serum 26 is needed for testing, a technician following the prior art manually breaks the tube, as shown in FIG. 6, and discards the clotted cell-containing part. The serum, as shown in FIG. 14, is then deposited into a collection container or cup 28.

The novel device which obviates the need for manual breaking of the tube is depicted in perspective in FIG. 7 and is denoted by the reference numeral 30 as a whole.

Cup 28, just mentioned, also appears in FIG. 7.

Although those skilled in the art of machine design will appreciate the fact that machine 30 may take many different forms, the preferred form includes a base part 32 from which the main body part 34 projects. The enlarged base 32 provides ample stability to the novel structure which is provided in table top form for the convenience of the medical personnel working with the tubes.

As is apparent from FIG. 7, base 32 is supported by suction cup members, collectively denoted 36, that are disposed at its corners. Other non-skid support devices are of course within the scope of this invention.

Base 32 includes a substantially imperforate bottom wall 38, upstanding front wall 40, side walls 42, 44 and rear wall 46 integrally formed therewith and projecting upwardly therefrom, and horizontally disposed top walls 48, 50 and 52.

Forward top wall 48 is suitably apertured as at 54 to slideably receive cup member 28 therein, as is perhaps best shown in FIG. 11. In lieu of such mounting, cup 28 could be held by opposing, flexible jaw members, not shown, which would project from wall 40 or other suitable surface of machine 30.

Drawer member 56, having handle 58, serves as a receptacle means that collects the ends of tubes that are cut off by the novel machine, as will be more fully set forth hereinafter.

The main body part 34 of device 30 includes four inclined side walls 60, 62, 64 and 66 and top wall 68. Top wall 68 is secured by screw members 70 to facilitate maintenance of the unit.

The leading end 72 of a bore means 74 (FIG. 8) is shown in FIG. 7, at the center of a hemispherical concavity 76 formed in wall 60; as suggested by the directional arrow 78 in FIG. 7, tube 10 or 14 is inserted into the bore means 74 when it is desired to cut said tube.

As perhaps best shown in FIG. 8, bore means 74 is formed in a boss means 80 that projects inwardly from front wall 60 and said bore means 74 extends the entire length of boss means 80. Concavity 76 helps guide the leading or clay 20-plugged end of tube 10 or 14 into bore means 74. In this embodiment, said leading end makes contact with the head 82 of spring-loaded rod member 84 and urges it in the direction of arrow 86; rod 84 is slideably mounted by a boss means 88 and a spring 90 or other suitable bias means is disposed in sandwiched relation between the annular upper edge 92 of said boss means 88 and said head member 82 of rod 84. Accordingly, rod 84 is biased in a direction opposite to arrow 86.

The trailing end 94 of rod 84 has a second head member 96 that contacts and displaces lever member 98 when the tube 10 or 14 is advanced. Lever 98 is biased in a direction opposite to arrow 86 but said bias is easily overcome by the technician; accordingly, advancing tube 10 or 14 results in depression of biased button 100 of microswitch 102 and the activation of a means for cutting tube 10 or 14. As shown in FIG. 8, the cutting blade member 104 is positioned at the trailing end of bore means 74.

FIGS. 8, 9 and 10 sequentially depict the novel mechanism in animation for overview purposes; the entire mechanism is shown in FIG. 11 but for introductory purposes the animation is helpful. As best understood by comparing FIGS. 8 and 9, once button 100 is depressed and normally open switch 102 is closed, link member 106 travels upwardly as indicated by arrow 108 in FIG. 9; such upward travel raises the trailing end of truncate link member 110 from its FIG. 8 to its elevated FIG. 9 position. Pin 112, as best shown in FIG. 9, travels in a slot means 114 formed in link member 110 to facilitate the vertical reciprocation of link 106.

The trailing end of a second truncate link member 118 is fixedly secured at pin 120 to the leading end of the first truncate link member 110, and the leading end of said second truncate link member 118 is pivotally secured to a plate 122 so that cutting blade 104 is driven downwardly into its FIG. 9 position when the truncate link members 110 and 118 rotate in a counterclockwise direction as indicated by directional arrow 124 in FIG. 9. Truncate link 118 and plate 122 are interconnected by pin 12 which reciprocates in slot 128.

The clotted cell-carrying distal end 138 of tube 14 is thus sheared by cutting blade member 104 as is clear from FIG. 9. The sheared end falls into drawer 56 as should be clear from FIG. 11.

As shown in FIG. 10, the shearing removal of said tubes' distal end 130 unloads spring 90 and rod 84 returns to its equilibrium position as denoted by the directional arrow 132. Simultaneously, lever 98 is unloaded by the retraction of head 96 of rod 84 and button 100 is thus released and microswitch 102 is restored to its normally open configuration.

Importantly, a spring member 134 or other suitable bias means extends between pin 138 on upstanding link 106 and pin 140 on plate 160 as shown in FIGS. 9 and 10; the upward travel of link 106, as denoted by arrow 108 in FIG. 9, overcomes the bias provided by spring 134, but once switch 102 is again open and the means for lifting link 106 is deactivated, spring 134 pulls link 106 downwardly to its FIG. 10 position as denoted by arrow 136 in FIG. 10.

Machine 10 is then ready to receive and cut additional microhematocrit tubes 10 or 14.

A more complete understanding of the device is provided in FIG. 11. There it will be seen that link 106 is fixedly secured by suitable means to the plunger 142 of a solenoid member 144. Solenoid 144 is conductively coupled by lines 146, 148 to microswitch 102 and a power source which may be AC as indicated by cord 150 at the lower right-hand corner of FIG. 11 or DC as indicated by battery pack 152. Thus, when current is applied to the coils of the solenoid 144, plunger 142 is drawn into the center of said coils and link 106 is pulled upwardly, easily overcoming the downward bias of spring 134.

As perhaps best understood in connection with FIG. 12, most of the parts just mentioned are mounted to a vertical wall 154 disposed within upper housing 34 of machine 10. For example, bracket 156 mounts switch 102 to the rearward side of said wall 154 and brackets 158, 160 on the forward side of wall 154 serve as mounting means for link members 110, 118 and their related parts.

On/off switch 162 cuts off power when unit 10 is not in use. As best understood in connection with FIGS. 12 and 13, there are actually two of said spring members 134, disposed on opposite sides of bracket 160; this arrangement prevents misalignment of the various moving parts of the novel device. There are also two link members 106 as well for the same reason.

Once the end 130 of a tube 10 or 14 has been sheared off, it falls into drawer 56 as aforesaid. As the drawer fills with tube parts, it is easily removed by pulling on handle 58; the drawer 56 slides atop ridges 55, 57, best shown in FIG. 11.

Importantly, the shearing of tube 10 or 14 takes place within the hollow cavity 161 defined by the walls of machine 10. Thus, glass shards and suspended particles of blood are substantially trapped within said cavity 161. Just as importantly, the technician need not manually break the tubes in the prior art manner depicted in FIG. 6.

After the distal end 130 has been sheared off, the technician deposits the serum into cup 28 as depicted in FIG. 14.

Machine 30 cuts each tube 10 or 14 inserted therein at the same place each time. Thus, it is adequate for use when a large plurality of tubes are to be broken and where each tube has about the same amount of clotted blood or red blood cells to be discarded.

However, patients differ. For example, a patient suffering from anemia will have less red blood cells and more serum than non-anemic patients. Accordingly, where a plurality of tubes are to be broken and where the length of the tube to be sheared off and discarded varies from tube to tube, use of machine 30 would result in inefficient capture of serum.

A machine that is not subject to the limitations of machine 30 is shown in part in FIGS. 15-17; the parts not shown in those Figs. are the same as in the first described embodiment, as indicated by the reference numerals.

As perhaps best shown in FIG. 17, a photoelectric cell including radiation source 169 disposed in housing 170 transmits a beam of suitable electromagnetic radiation 172 to detector means 174. Beam 172 travels through opening 176 formed in boss member 80 as shown when no tube 10 or 14 is inserted into bore means 74. As long as detection means 174 detects the presence of radiation, microswitch 102 remains in its normally open condition.

However, when beam 172 is interrupted, detection member 174 sends an electrical signal to a relay means or a suitable equivalent thereof, not shown. Such interruption occurs when the clay-filled end of a tube blocks beam 172 and when the clotted blood cells or red blood cells collected thereatop follow. Then, when the substantially opaque clay and red blood cells or clotted blood cells have traveled past beam 172 and the clear serum is disposed in the path of beam 172, detection means 174 is again activated. It sends an electrical signal to the relay means and the relay means then sends a signal to microswitch 102, thereby activating it and causing the above-described sequence to follow. An animation of the sequence appears in FIGS. 15-17.

Since cutting blade 104 is not activated until the relay means receives its second signal, tubes having widely varying amounts of serum therein are cut at the optimal location, i.e., at the line of demarcation between opaque and transparent materials.

It will be observed in FIGS. 15-17 that radiation source 169 is positioned inwardly relative to the trailing end of boss 80. Therefor, to cause a tube to be cut even closer to the line of demarcation, source 169 could be moved further to the right in the Figs. to a point almost aligned with the cutting edge of cutting blade 104.

Machine designers, now that the invention has been disclosed, could make numerous changes to the specific structure shown herein, but such changes that are within the ordinary skill of machine designers are within the scope of this invention.

Clearly, this invention pioneers the art of machines for cutting microhematocrit tubes and other tubes as well. Thus, it is a pioneering invention and the claims that follow are entitled to broad interpretation as a matter of law.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:
1. A machine for cutting microhematocrit tubes, comprising:
   a hollow housing member;
   said housing member having a bottom wall, a top wall, and side walls;
   said walls collectively defining an interior cavity means that substantially separates air therewithin from the environment exterior to said housing member;
   a reciprocally mounted cutting blade member being disposed within said interior cavity means;
   an aperture means formed in a preselected wall of said housing member to admit a tube into said cavity means;
   means for activating said cutting blade member when a tube is inserted into said cavity means;
   a boss means formed on an interior surface of said preselected wall;
   said boss means projecting into said interior cavity means;
   a bore means formed in said boss means, said bore means having a predetermined length coextensive with a predetermined extent of said boss means;

said bore means having a diameter only slightly greater than the outer diameter of a tube to be inserted thereinto;

said bore means having an outer end in open communication with said aperture means formed in said preselected wall;

a concavity formed in said preselected wall in surrounding relation to said outer end of said bore means for guiding a tube to be inserted into said bore means;

said predetermined length of said bore means being less than the length of a tube to be cut by said machine;

said predetermined length of said bore means being sufficiently long in relation to the outer diameter of said tube and the diameter of said bore means to substantially prevent droplets of particles from traversing the extent of said bore means, thereby ensuring that said droplets are confined within said housing member;

said cutting blade member being disposed at an inner end of said bore means so that a tube extending into said cavity means from said bore means is sheared when said cutting blade member is activated.

2. The machine of claim 1, wherein said means for activating said cutting blade member includes a switch means that is tripped by a tube inserted into said cavity means.

3. The machine of claim 2, wherein said means for activating said cutting blade member further includes a solenoid member conductively coupled to said switch means, said solenoid member including a plunger means retractable thereinto upon current flow through said solenoid member, and said means for activating said cutting blade member further including a rigid link member disposed in interconnecting relation between said plunger means and said cutting blade member.

* * * * *